United States Patent
Russell et al.

(10) Patent No.: US 9,265,925 B2
(45) Date of Patent: Feb. 23, 2016

(54) CONTROLLING FLOW IN A MEDICAL INJECTION SYSTEM

(71) Applicant: ACIST Medical Systems, Inc., Eden Prairie, MN (US)

(72) Inventors: John Russell, Cologne, MN (US); Troy Marshall Coolidge, Victoria, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 508 days.

(21) Appl. No.: 13/652,746

(22) Filed: Oct. 16, 2012

(65) Prior Publication Data
US 2014/0107611 A1    Apr. 17, 2014

(51) Int. Cl.
*A61M 39/28* (2006.01)
*A61M 5/168* (2006.01)
*F16K 7/06* (2006.01)
*A61M 5/142* (2006.01)
*A61M 5/00* (2006.01)

(52) U.S. Cl.
CPC .......... *A61M 39/28* (2013.01); *A61M 5/14216* (2013.01); *A61M 5/16813* (2013.01); *A61M 39/285* (2013.01); *F16K 7/063* (2013.01); *F16K 7/065* (2013.01); *A61M 5/007* (2013.01)

(58) Field of Classification Search
CPC . A61M 39/28; A61M 39/284; A61M 39/285; F16K 7/065; F16K 7/063; F16K 7/066; F16K 31/52491; B01L 2400/0655
USPC .................................................. 251/4, 6, 9
See application file for complete search history.

(56) References Cited

U.S. PATENT DOCUMENTS

| 2,985,182 | A | * | 5/1961 | Williams | ........................ 137/85 |
| 3,299,904 | A | | 1/1967 | Burke | |
| 3,411,534 | A | * | 11/1968 | Rose | ............................ 137/595 |
| 3,802,463 | A | | 4/1974 | Dabney | |

(Continued)

FOREIGN PATENT DOCUMENTS

| GB | 2274326 A | 7/1994 |
| WO | 0155626 A1 | 8/2001 |

OTHER PUBLICATIONS

International Searching Authority, Invitation to Pay Additional Fees and, Where Applicable, Protest Fee, Communication Relating to the Results of the Partial International Search, (co-pending) International Application No. PCT/US2012/060380; Aug. 1, 2013, 7 pages, European Patent Office, Rijswijk, The Netherlands.

*Primary Examiner* — Kevin C Sirmons
*Assistant Examiner* — William Carpenter
(74) *Attorney, Agent, or Firm* — Fredrikson & Byron P.A.

(57) ABSTRACT

A valve apparatus for a medical injection system includes a pinching member and at least one spring-loaded anvil. A tubing line of the injection system may be positioned between the pinching member and the anvil, such that when the pinching member is moved into a pinching position adjacent to the anvil, for example, by rotation of a shaft to which the member is coupled, the pinching member compresses the tubing line against the spring-loaded anvil. The pinching member is preferably rotatable about an auxiliary axis, which is eccentric, or offset from a central axis of the shaft. A spring member of the spring-loaded anvil is preferably pre-loaded. In certain applications, the pinching member, when moved into the pinching position, applies a pinching force of greater than approximately 45 pounds, for example, to prevent flow through the tubing line at an injection pressure of up to approximately 1200 psi.

11 Claims, 8 Drawing Sheets

(56) References Cited

U.S. PATENT DOCUMENTS

| | | | |
|---|---|---|---|
| 3,813,077 A | 5/1974 | Kolic | |
| 3,861,421 A * | 1/1975 | Thompson | F16K 7/06 |
| | | | 137/636.4 |
| 3,918,490 A * | 11/1975 | Goda | 137/597 |
| 4,061,142 A * | 12/1977 | Tuttle | 604/34 |
| 4,282,902 A * | 8/1981 | Haynes | F16K 7/065 |
| | | | 137/595 |
| 4,484,599 A | 11/1984 | Hanover et al. | |
| 4,585,442 A * | 4/1986 | Mannes | A61M 39/284 |
| | | | 251/7 |
| 4,645,489 A * | 2/1987 | Krumme | A61M 39/285 |
| | | | 251/11 |
| 4,969,486 A | 11/1990 | Puzio | |
| 5,113,906 A | 5/1992 | Hogner | |
| 5,117,870 A | 6/1992 | Goodale | |
| 5,458,581 A | 10/1995 | Hull | |
| 5,769,385 A * | 6/1998 | Burrous et al. | 251/7 |
| 5,901,745 A * | 5/1999 | Buchtel | 137/595 |
| 8,152,780 B2 | 4/2012 | Evans et al. | |
| 2003/0127613 A1* | 7/2003 | Pfeil et al. | 251/9 |
| 2005/0053501 A1* | 3/2005 | Akahori | 417/474 |
| 2005/0255426 A1 | 11/2005 | Mariaulle | |

\* cited by examiner

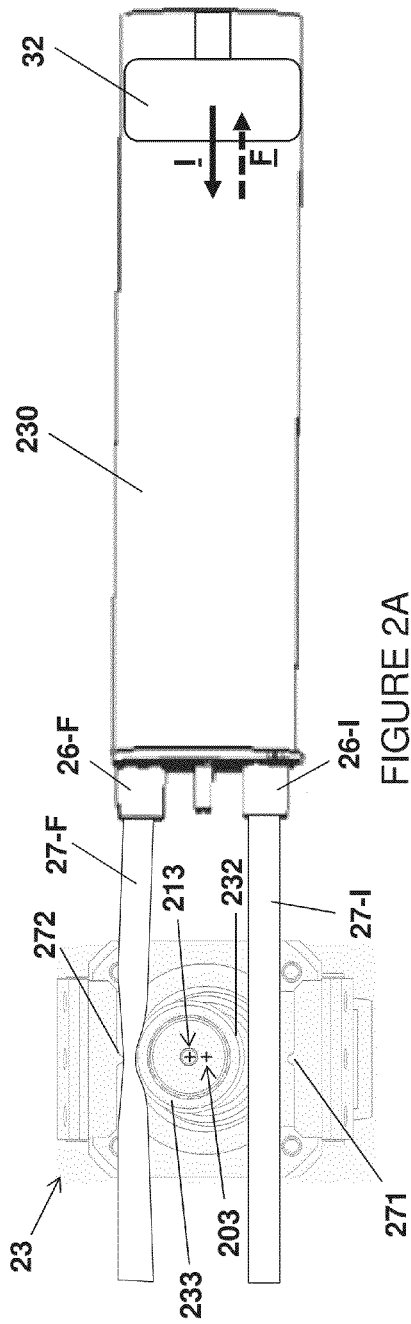
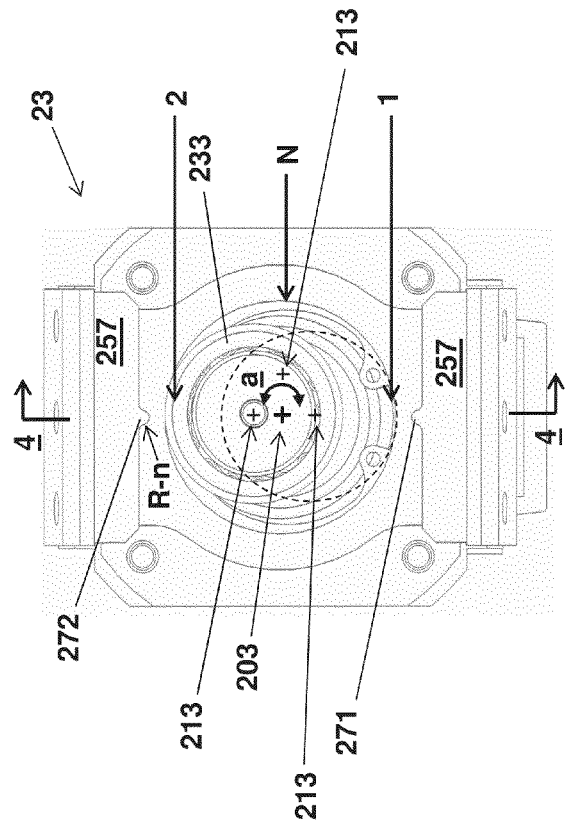
FIGURE 2A
FIGURE 2B

CONTROLLING FLOW IN A MEDICAL INJECTION SYSTEM

TECHNICAL FIELD

The present disclosure pertains to medical injection systems and more particularly to apparatus and methods for controlling flow therein.

BACKGROUND

FIG. 1A is a perspective view of an exemplary medical injection system 100 (the ACIST CV$_i$® system) for delivering a contrast agent into a patient's vascular system for medical imaging. FIG. 1A illustrates a first fluid reservoir 132 for supplying a syringe-type positive displacement pump of a pressurizing unit 130, via a fill tubing line 27-F, and an injection tubing line 27-I coupled to unit 130 for injection of, for example, a radiopaque contrast agent, into a patient's vascular system via an inserted catheter (not shown), for example, coupled to a patient tubing line 122 at a connector 120 thereof. FIG. 1A further illustrates a second fluid reservoir 138 from which a diluent, such as saline, is drawn by a peristaltic pump 106 through yet another tubing line 128 that feeds into tubing line 122. A manifold valve 124 and associated sensor 114 control the flow of fluids into tubing line 122, from pressurizing unit 130 and from tubing line 128.

Although not shown in FIG. 1, the syringe-type positive displacement pump of unit 130 includes a fill port and an injection port to which tubing lines 27-F and 27-I, respectively are coupled; a check valve (not shown) in line 27-F and valve 124 in line 27-I are employed to control flow through tubing lines 27-F and 27-I. For example, when the pump of unit 130 is activated to draw in fluid from reservoir 132, flow from tubing lines 122 and 128 through injection tubing line 27-I is blocked by valve 124; and, after the pump is filled, when the pump is activated to pressurize the fluid therein, valve 124 is opened to allow flow of the pressurized fluid through line 27-I and into line 122, while flow through fill tubing line 27-F is blocked by the aforementioned check valve. A variety of alternative valve mechanisms for controlling the flow through tubing lines of medical injection systems, such as tubing lines 27-F and 27-I of injection system 100, are known in the art. For example, a suitable pinch valve apparatus is described in commonly-assigned U.S. Pat. No. 8,152,780. Yet, there is still a need for improved valve apparatus that simplify and increase the efficiency of valve operation to control flow in medical injection systems.

SUMMARY

Apparatus and methods of the present invention are directed toward controlling flow through one or more tubing lines of a medical injection system. According to some methods, which may be employed by an injection system that includes fill and injection tubing lines coupled a pump, the two tubing lines are positioned in a valve apparatus such that a first of the two lines is located between a pinching member of the apparatus and a spring-loaded anvil of the apparatus, and a second of the two lines is located between the pinching member and a second spring-loaded anvil of the apparatus; subsequently, the pinching member is moved from a first position, at which the pinching member compresses the first tubing line against the first spring-loaded anvil, to a second position, at which the pinching member compresses the second tubing line against the second spring-loaded anvil, and vice versa. When the pinching member compresses the first tubing line, flow therethrough is blocked while the pump draws fluid in through the second tubing line; and, when the pinching member compresses the second tubing line, flow therethrough is blocked while the pump injects the fluid out through the first tubing line, for example, at an injection pressure of up to approximately 1200 psi, according to some embodiments and methods. In alternative injection systems, a single tubing line may be positioned in a similar valve assembly that includes only one spring-loaded anvil in conjunction with the pinching member.

According to some preferred embodiments, the pinching member is coupled to a rotatable shaft, for example, driven by a motor that moves the pinching member about a central axis of the shaft between the first and second positions, and through a neutral position therebetween (where the pinching member may be located when the tubing lines are initially positioned in the valve apparatus). Furthermore, the pinching member is preferably rotatable about an auxiliary axis, which is eccentric, or offset from the central axis of the shaft, so that pinching member rolls into and out of contact with the tubing lines when moved back and forth between the first and second positions. A spring member of each of the spring-loaded anvils may be in the form of an elongate flexure that has a fixed end and a floating end, to which an anvil block, on which the corresponding anvil is formed, is attached. According to some preferred methods and embodiments, each spring-member is pre-loaded, for example, prior to moving the pinching member to compress one of the tubing lines in the valve apparatus. Furthermore, a minimum gap between each pre-loaded spring-loaded anvil and the pinching member in one or both of the first and second positions is preferably established for an approximate 20% squeeze reduction of the wall thickness of the corresponding tubing line minus a maximum in-service deflection of the corresponding pre-loaded spring member, which in-service deflection is preferably established, for a given spring constant of the pre-loaded spring member, to provide a pinching force of greater than approximately 45 pounds, with a variability within approximately 15% of nominal, over the range of in-service deflection.

BRIEF DESCRIPTION OF THE DRAWINGS

The following drawings are illustrative of particular methods and embodiments of the present disclosure and, therefore, do not limit the scope of the invention. The drawings are not to scale (unless so stated) and are intended for use in conjunction with the explanations in the following detailed description. Methods and embodiments will hereinafter be described in conjunction with the appended drawings, wherein like numerals denote like elements, and:

FIG. 2A is a plan view of fill and injection tubing lines that extend from a positive displacement pump and through a valve apparatus, according to some embodiments and methods of the present invention;

FIG. 2B is an enlarged plan view of the apparatus of FIG. 2A, according to some embodiments;

DETAILED DESCRIPTION

The following detailed description is exemplary in nature and is not intended to limit the scope, applicability, or configuration of the invention in any way. Rather, the following description provides practical illustrations for implementing exemplary methods and embodiments. Examples of constructions, materials and dimensions are provided for selected elements, and all other elements employ that which is known to those of skill in the field of the invention. Those skilled in the art will recognize that many of the examples provided have suitable alternatives that can be utilized.

Figure 1A:
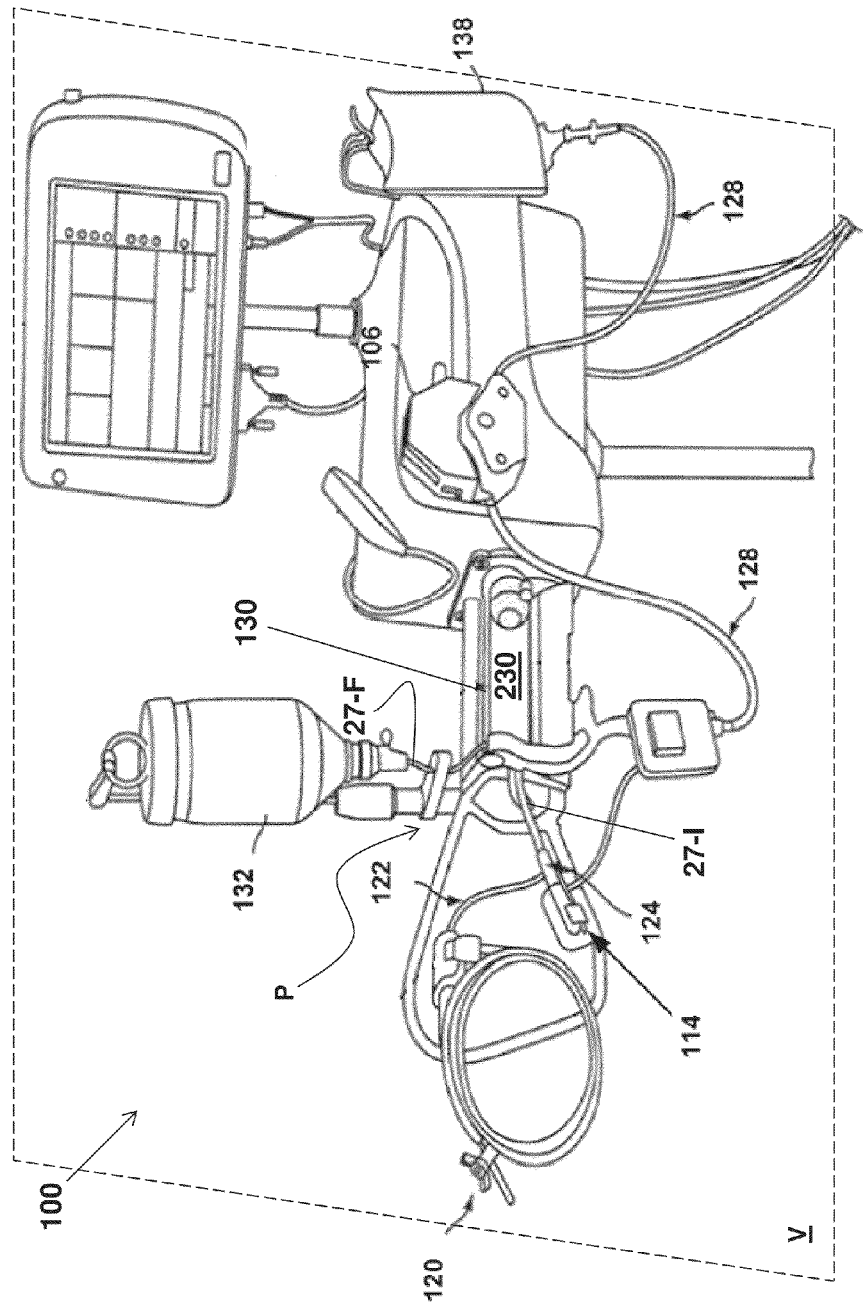
FIGS. 1A-B are perspective views of at least portions of exemplary medical injection systems that may employ embodiments of the present invention.

FIG. 2A is a plan view of a portion of fill tubing line 27-F and a portion of injection tubing line 27-I, both of which extend from a positive displacement pump 230 and through a valve apparatus 23, according to some embodiments and methods of the present invention. Fill tubing line 27-F is shown coupled to a fill port 26-F of pump 230 and injection line 27-I to an injection port 26-I of pump 230. With reference back to FIG. 1A, it may be appreciated that pump 230 may be employed by, and integrated into pressurizing unit 130 of system 100, and valve apparatus 23 may be employed in system 100, to take over for the aforementioned check valve and manifold valve 124 by controlling flow through lines 27-F and 27-I. FIG. 2A illustrates valve apparatus 23 including a pinching member 233, a first spring-loaded anvil 271, and a second spring-loaded anvil 272; injection tubing line 27-I is shown extending between first anvil 271 and pinching member 233, and fill tubing line 27-F between second anvil 272 and pinching member 233. Each of tubing lines 27-F, 27-I may be formed from a nylon reinforced polyurethane or a flexible PVC material, both of which are known to those skilled in the art. In FIG. 2A, pinching member 233 compresses fill tubing line 27-F against spring-loaded anvil 272 to block a flow of fluid therethrough from pump 230, when a plunger 32 of pump 230 moves per arrow I to pressurize and inject the fluid out through injection tubing line 27-I. FIG. 2A further illustrates pinching member 233 being coupled to a shaft 232, which is preferably rotatable about a central axis 203 thereof, for example, back and forth according to double-headed arrow a of FIG. 2B, to move member 233 between first and second positions 1, 2.

FIG. 2B is an enlarged plan view of valve apparatus 23, wherein dashed lines indicate first position 1 of pinching member 233, prior to movement to second position 2, which is the same as that illustrated in FIG. 2A. FIGS. 2A-B illustrate pinching member 233 being centered on an auxiliary axis 213, which is eccentric, or offset from central axis 203. With further reference to FIG. 2B, a rotation of shaft 232, to move pinching member 233 between first position 1 and second position 2, through a neutral position N, is illustrated by three locations of auxiliary axis 213. It may be appreciated that, according to preferred methods of the present invention, pinching member 233 is initially located in neutral position N when pump 230 and tubing lines 27-F, 27-I are loaded into an injection system, for example, to increase the ease of positioning lines 27-F and 27-I between pinching member 233 and the corresponding spring-loaded anvil 271, 272 within valve apparatus 23. Then, once pump 230 and lines 27-F, 27-I are loaded, pinching member 233 is moved into first position 1 to block flow from line 27-I, before plunger 32 of pump 230 is moved, per arrow F (FIG. 2A), to draw fluid in through tubing line 27-F. After plunger 32 draws a predetermined volume of fluid into pump 230, pinching member 233 is moved from first position 1 to second position 2, as illustrated in FIG. 2A, to block flow through tubing line 27-F while pump 230 expels the fluid through line 27-I, for example, at an injection pressure of up to approximately 1200 psi.

Figure 1B:
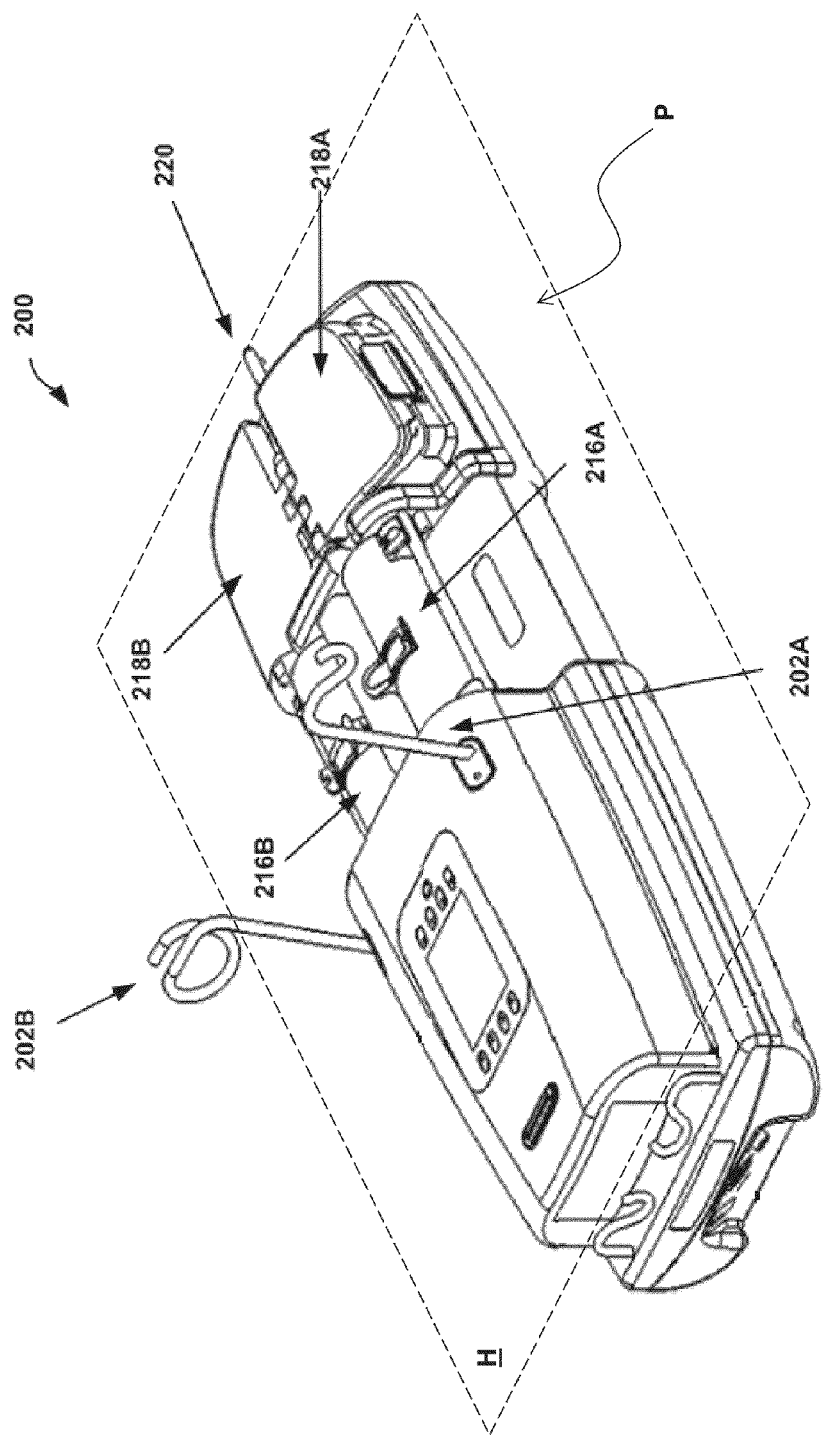
Figure 3:
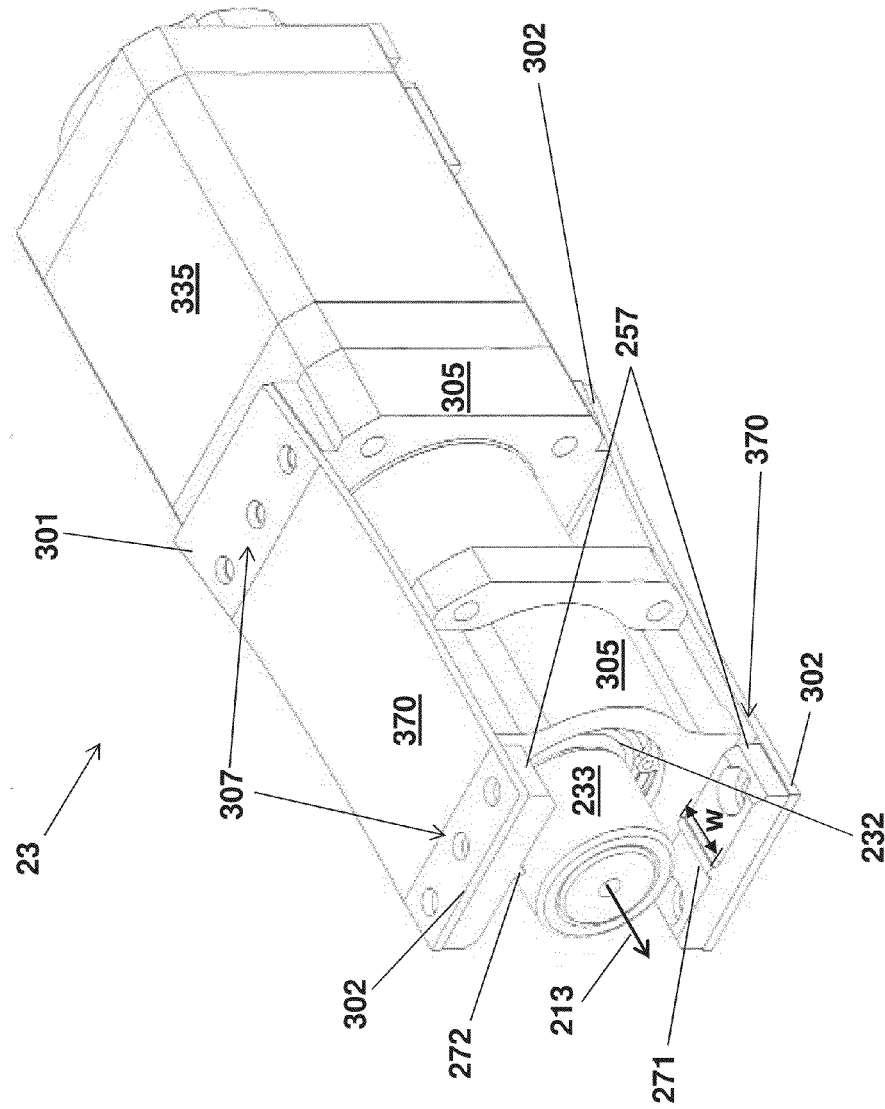
FIG. 3 is a perspective view of the valve apparatus, according to some embodiments.
Figure 4A:
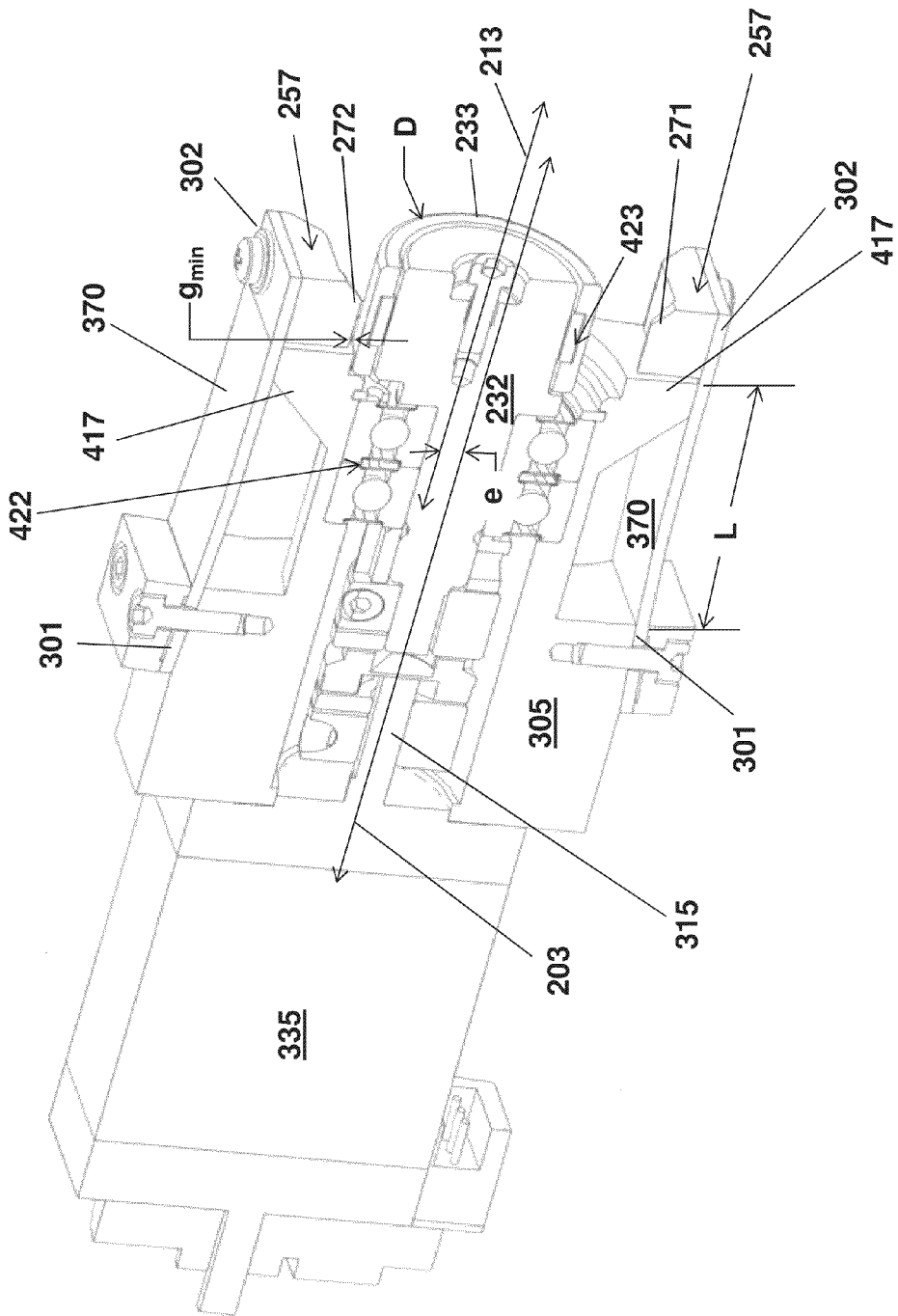
FIG. 4A is a longitudinal cross-section view through section line 4-4 of FIG. 2B, according to some embodiments.

FIG. 3 is a perspective view of valve apparatus 23, according to some embodiments. FIG. 3 illustrates shaft 232 supported in a structure 305, for example, by a ball bearing assembly 422, which may be seen in the cross-section view of FIG. 4A. FIG. 4A is a longitudinal cross-section view through section line 4-4 of FIG. 2B, according to some embodiments. FIG. 4A further illustrates shaft 232 being coupled to a shaft 315 of a motor 335, for example, a stepping motor (i.e. Item #PK235PDA described at http://catalog.orientalmotor.com), which is contained in a fixed housing of valve apparatus 23. With reference back to FIG. 1A, and as alluded to above, valve apparatus 23 may be employed by system 100, for example, by mounting apparatus 23 in the general vicinity indicated by reference letter P so that motor 335 sits to the rear of a generally vertical plane V, in which fill and injection ports 26-F, 26-I of pump 230 lie, and shaft 232 extends toward tubing lines 27-F, 27-I; thus, lines 27-F, 27-I may be positioned in valve apparatus 23 as illustrated in FIG. 2A. Furthermore, with reference to FIG. 1B, an injection system 200, which has an alternative configuration, may employ a pair of valve apparatus 23. FIG. 1B illustrates system 200 including a pair of sleeves 216A, 216B, each of which may house a pump like pump 230 (FIG. 2A), such that a set of tubing lines 27-F, 27-I, which are routed from each pump within a corresponding compartment 218A, 218B, lie in a generally horizontal plane H. According to the illustrated embodiment, one of the two pumps may pump saline, for example, filled form a reservoir mounted on a fixture 202A, and another of the pumps may pump a contrast agent, for example, filled from a reservoir mounted on a fixture 202B; a guide 220 is shown extending from compartments 218A, 218B for connecting the saline and contrast injection lines to a patient line. With further reference to FIG. 1B, motor 335 of each valve apparatus 23 employed by system 200 may be mounted in the general vicinity indicated by reference letter P, below plane H, so that shaft 232 of each extends toward the corresponding set of tubing lines 27-F, 27-I; thus, each set of tubing lines may be positioned in the corresponding valve apparatus 23 as illustrated in FIG. 2A.

Motor 335 of valve apparatus 23, when actuated (i.e. either user-actuated, or actuated in response to a trigger signal from a sensor coupled to pump 230), drives shaft 232 with sufficient torque to force pinching member 233, either into position 1, to compress tubing line 27-I against spring-loaded anvil 271, or into position 2, to compress tubing line 27-F against spring-loaded anvil 272, and thereby effectively block flow through lines 27-I and 27-F, in succession. As was generally described above, once tubing lines 27-I, 27-F are positioned in valve assembly 23, motor 335 may be actuated to move pinching member 233 to first position 1, at which member 233 compresses tubing line 27-I against anvil 271, while pump 230 draws in fluid from a reservoir, for example, reservoir 132 of FIG. 1, through tubing line 27-F; then, once pump 230 is filled, motor is actuated to move pinching member 233 to second position 2 in order to compress tubing line 27-F while pump injects the fluid through tubing line 27-I. Over the course of one or more imaging procedures, pump 230 may need to be filled as many as approximately 5 times up to approximately 25 times; thus pinching member 233 is repeatedly moved between first and second positions 1, 2 enough times to replenish the volume of pump 230 and thereby support the required number of injections. According to some preferred methods, motor 335 drives shaft back and forth through neutral position N, approximately 180 degrees about central axis 203, to move pinching member 233, between first and second positions 1, 2; alternatively, motor 335 may drive shaft 232 360 degrees around central axis 203 to move pinching member 233 between first and second positions 1, 2. The stepping motor preferably includes an encoder to monitor the steps of the rotation of shaft 232 in order to keep track of, and confirm the position of pinching member 233 during system operation.

FIG. 3 further illustrates each of anvils 271, 272 spring-loaded by virtue of attachment to a corresponding spring member, each of which is in the form of an elongate flexure 370. FIG. 3 illustrates a first end 301 of each flexure 370 attached to support structure 305, and each of anvils 271, 272 being formed on a corresponding anvil block 257, which is fastened to a floating second end 302 of the corresponding flexure 370. Reference numeral 307 designates locations for exemplary fasteners, some of which may be seen in FIG. 4A. Each of anvils 271, 272 preferably extends over a width w that is greater than or equal to an outer diameter of each of tubing lines 27-F, 27-I, and each may have a radius R-n of between approximately 0.06 inch (1.5 mm) and approximately 0.08 inch (2 mm), for example, to effectively pinch tubing lines 27-I, 27-F without damaging the walls thereof by applying undue stress. Anvil blocks 257 are preferably formed from stainless steel.

With further reference to FIGS. 2B and 4A, for a given wall thickness and material properties of the tubes forming tubing lines 27-F, 27-I, a minimum gap $g_{min}$ is established between pinching member 233 and each of anvils 271, 272. ($g_{min}$ is shown between second anvil 272 and member 233 in second position 2.) When tubing lines, for example, lines 27-I and 27-F, are positioned within valve apparatus 23, for example as illustrated in FIG. 2A, the spring loading provided by flexures 370 establishes a relatively constant pinching pressure between each of anvils 271, 272 and pinching member 233 in the first and second positions 1, 2, respectively, for example, across a standard tolerance range wall thickness for the tubing forming each of tubing lines 27-I, 27-F. Furthermore, the spring loading of anvils 271, 272 maintains the relatively constant pinching pressure if the stiffness of either tubing line 27-I, 27-F creeps/declines in response to multiple pinch cycles, for example, up to as many as approximately 25 cycles, which may take place over the course of an imaging procedure, or a day of multiple imaging procedures, as described above.

With reference back to FIG. 4A, according to some preferred methods and embodiments, flexures 370 are pre-loaded to establish a desired pinching force applied by pinching member 233, and to reduce an amplitude of cyclic loading seen by each flexure 370 over the life of valve apparatus 23, for example, corresponding to up to approximately 60,000 pinch cycles. FIG. 4A illustrates pre-load supports 417, each of which is preferably formed in support structure 305; each support 417 is located adjacent anvil block 257 at floating second end 302 of the corresponding elongate flexure 370.

FIG. 4A further illustrates pinching member 233 supported by a needle bearing assembly 423, such that member 233 is rotatable around auxiliary axis 213. Such support is preferred to allow pinching member 233 to roll into and out of contact with tubing lines 27-F, 27-I, thereby facilitating the movement of pinching member into, and out from first and second positions 1, 2 without displacing the corresponding tubing line 27-F, 27-I along a direction of its longitudinal axis, and/or without undue wear on tubing lines 27-F, 27-I.

EXAMPLE

According to an exemplary embodiment, each tubing line 27-I, 27-F is formed by a nylon-reinforced polyurethane tube having a nominal outer diameter of approximately 0.188 inch (4.78 mm) and a nominal wall thickness t of approximately 0.05 inch (1.27 mm). Pinching member 233 and each spring-loaded anvil 271, 272 are suitably dimensioned, supported and arranged in valve apparatus 23 so that member 233 and each anvil 271, 272 apply a sufficient pinching force to each of the exemplary tubing lines 27-I, 27-F, when each tubing line is positioned in valve apparatus 23 (i.e. per FIG. 2A), and when member 233 is in the first and second positions 1, 2, respectively. The sufficient pinching force, which prevents flow through the exemplary tubing lines at a maximum injection pressure of approximately 1200 psi has been found to be approximately 45 pounds, but, in order to assure a tubing failure (i.e. burst at approximately 1500 psi) prior to a cracking/leak through the pinching of fill tubing line 27-F, between pinching member 233 and spring-loaded anvil 272, at injection pressures exceeding the 1200 psi, a safety margin of 10 pounds brings the pinching force to approximately 55 pounds for the exemplary embodiment. Thus, prevention of backflow through fill tubing line 27-F is assured during injections through injection tubing line 27-I. Furthermore, in the exemplary embodiment, the aforementioned exemplary stepping motor (Item #PK235PDA; http://catalog.orientalmotor.com), which operates according to the torque curve shown in FIG. 5A, applies sufficient torque, via shafts 315 and 232, to repeatedly move pinching member 233 from first position 1 to second position 2, and vice versa, without stalling, when the aforementioned tubes for each tubing line 27-I, 27-F are positioned in valve apparatus 23.

Figure 4B:
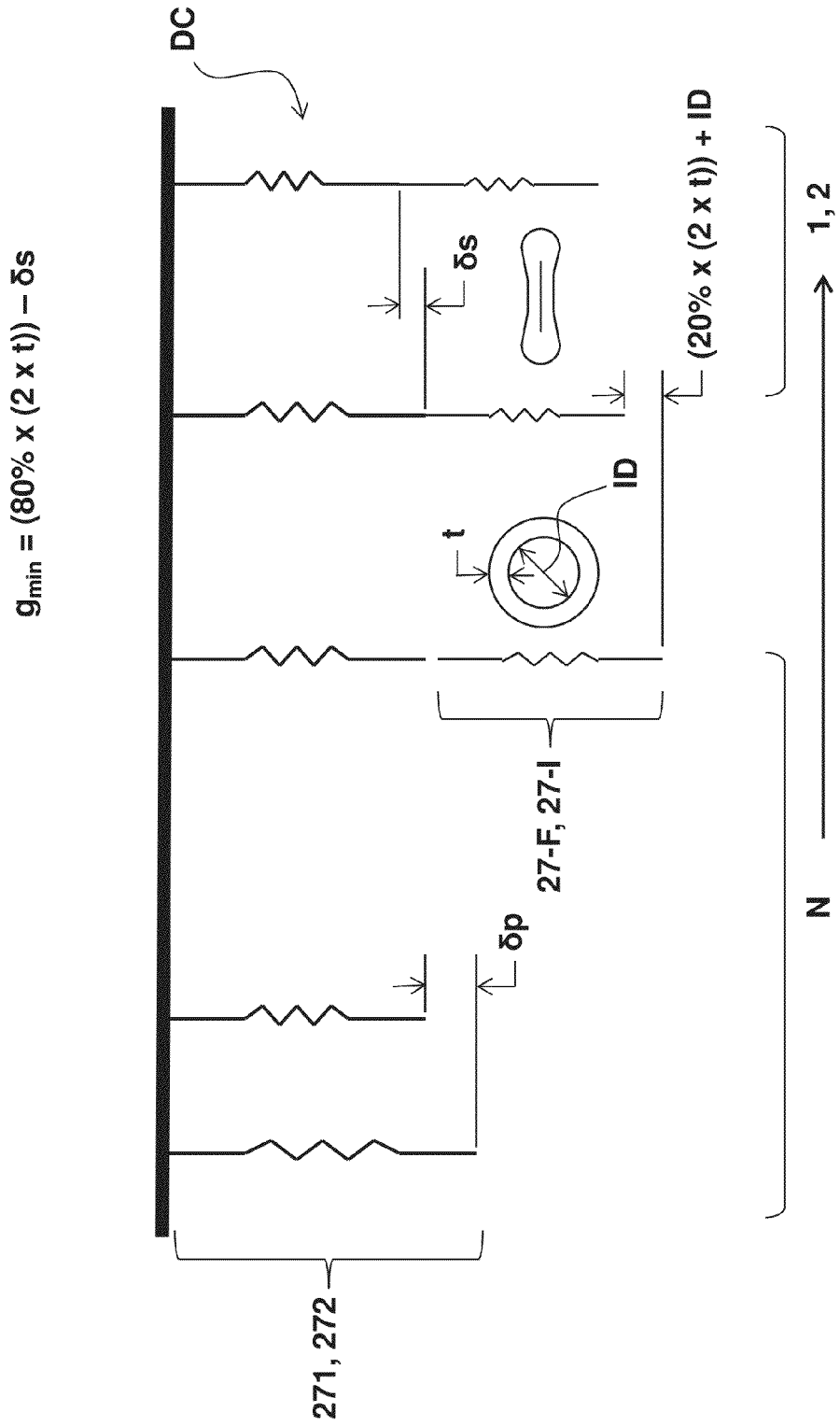
FIG. 4B is a schematic representation of an exemplary valve apparatus in which schematic spring elements are employed.

With reference to FIG. 4A, each exemplary elongate flexure 370 is formed from a fully hardened stainless steel strip, which has a spring constant of approximately 439 lb/in; and each flexure 370 extends between the corresponding fixed end 301 and the corresponding anvil block 257, over a length L, which is approximately 1.42 inch. The minimum gap $g_{min}$, which is between first anvil 271 and pinching member 233, when member 233 is in first position 1 (FIG. 2B), and between second anvil 272 and pinching member 233, when member is in second position 2, as shown in FIG. 4A, is set to approximately 0.05 inch (1.27 mm) for the exemplary embodiment. With reference to the schematic shown in FIG. 4B, this minimum gap $g_{min}$ is established according to a desired 20% squeeze reduction of the wall thickness t of each of tubing lines 27-I, 27-F and according to a maximum in-service deflection δs of spring-loaded anvils 271, 272, which is approximately 0.03 inch (0.76 mm). FIG. 4B illustrates a deflection of tubing lines 27-F, 27-I equal to the 20% reduction plus an inner diameter ID of each tubing line. FIG. 4B further illustrates a pre-load deflection δp, which, when established at approximately 0.09 inch for each spring-loaded anvil 271, 272, for example, by pre-load supports 417 abutting each exemplary flexure 370 (FIG. 4A), assures that a radial force $F_R$ (shown in the schematic of FIG. 5B), applied to positioned tubing lines 27-I, 27-F by each of spring-loaded anvils 271, 272, with pinching member 233 positioned in the first and second positions 1, 2, respectively, is approximately maintained at the aforementioned 55 pound pinching force. It should be noted that FIG. 4B illustrates spring-loaded anvils 271, 272 and tubing lines 27-F, 27-I as schematic spring elements transitioning in response to deflections imposed by pre-loading and by movement of pinching member 233 from the above-described neutral position N and into one of the above-described first and second positions 1, 2, wherein pinching member 233 is at top or bottom dead center DC when the maximum in-service deflection δs is achieved. According to preferred embodiments, the spring constant of flexures 370, minimum gap $g_{min}$ and pre-load deflection δp determine a maximum in-service deflection δs, for the 20% squeeze reduction, that limits a variation in the 55 pound pinching force, for example, to within approximately 15% of nominal, throughout the range of in-service deflection δs (i.e. from initial compression of each tubing line 27-F, 27-I to top dead center DC).

Figure 5A:
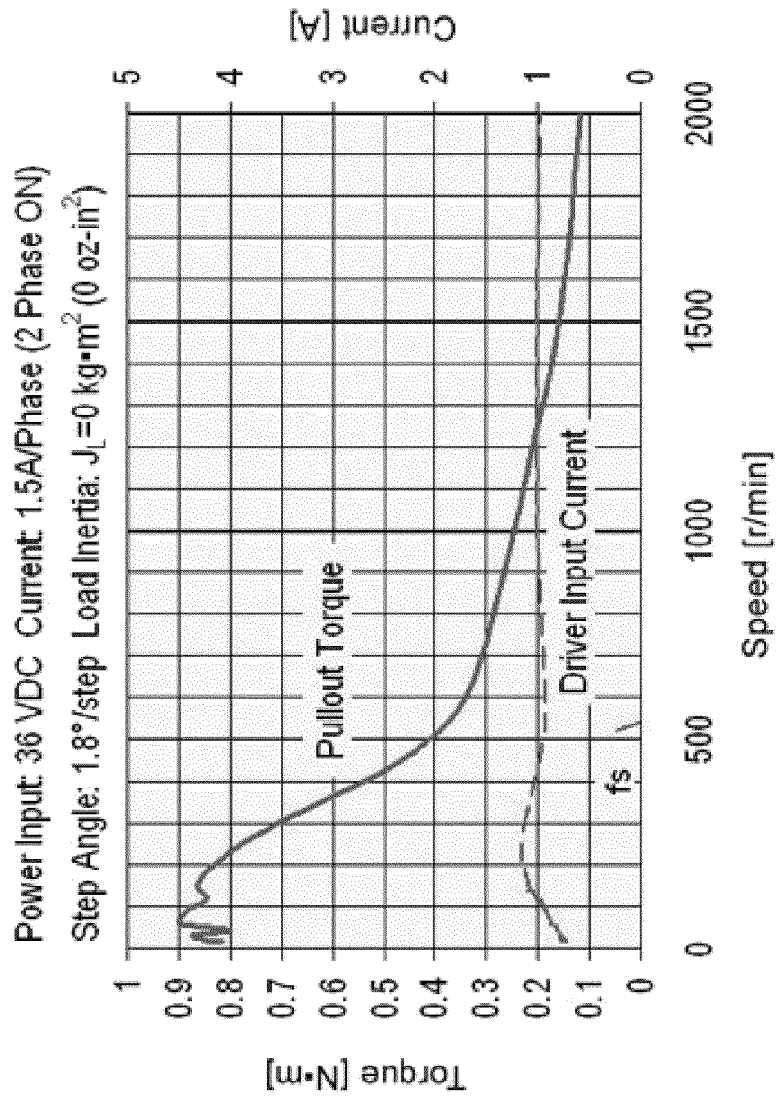
FIG. 5A is a chart defining torque output of a suitable stepping motor, according to some embodiments.
Figure 5B:
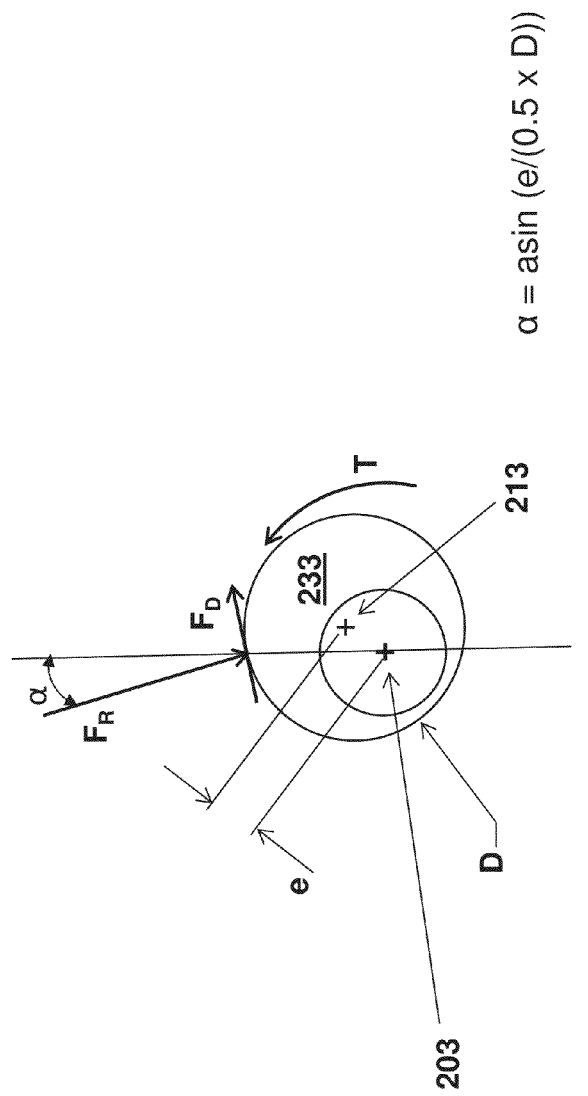
FIG. 5B is another schematic for reference in conjunction with description of the exemplary valve apparatus.

FIG. 5B is a schematic demonstrating how a diameter D of pinching member 233 and an offset e, in conjunction with radial force $F_R$ and a drag force $F_D$, dictate the torque necessary to move member 233 into first and second positions 1, 2 (FIG. 2B). The aforementioned pre-load deflection δp, along with a maximum rolling friction coefficient μ of approximately 0.005, for needle bearing assembly 423 with respect to a perimeter of pinching member 233, helps to limit the drag force $F_D$ on pinching member 233 as member 233 rolls into contact with each of positioned tubing lines 27-F, 27-I. Furthermore, diameter D of pinching member 233, which is set to approximately 1.1 inch (28 mm), and offset e of auxiliary axis 213 from central axis 203, which is set to approximately 0.118 inch (3 mm), establish a maximum pressure angle α of approximately 12.4 degrees, which also contributes to limiting the drag force $F_D$. Equations for both the maximum pressure angle and the drag force are shown in FIG. 5B, as is the equation governing the maximum torque T required to move pinching member 233 into the first and second positions 1, 2. Thus, according to the exemplary embodiment, the aforementioned stepping motor, performing according to the torque curve shown in FIG. 5A, is able to repeatedly move pinching member 233 into the first and second positions 1, 2, at which the aforementioned pinching force is applied to each tubing line 27-I, 27-F, respectively. Furthermore, the motor may drive shaft 232 at a speed to move pinching member 233 from neutral position N to either of the first and second positions 1, 2, within a time of approximately 250 milliseconds. Preferably, the motor moves pinching member 233 back and forth, through 180 degrees, between the first and second positions 1, 2, as described above in conjunction with FIG. 2B; but this exemplary embodiment does not rule out 360 degree movement of pinching member 233.

Finally, it should be noted that embodiments of the disclosed valve apparatus may be employed to control flow only through injection lines, for example, in systems that do not require pump filling and the associated fill tubing lines. In this context, the above-described embodiments may operate to control flow through two injection lines, successively, by moving back and forth between the two positions 1, 2, or may operate to control flow in a single injection line, for example, by only moving between the neutral position N and the first position 1.

In the foregoing detailed description, the invention has been described with reference to specific embodiments. However, it may be appreciated that various modifications and changes can be made without departing from the scope of the invention as set forth in the appended claims.

We claim:

1. A valve apparatus for controlling flow through a pair of tubing lines of a medical injection system, the apparatus comprising:
   a rotatable shaft;
   a pinching member coupled to the rotatable shaft such that the pinching member moves around a central axis of the shaft when the shaft is rotated;
   a first anvil attached to a first spring member and located on a first side of the shaft; and
   a second anvil attached to a second spring member and located on a second side of the shaft, the second side being generally opposite the first side;
   wherein rotation of the shaft moves the pinching member from a first position, adjacent to the first anvil, to a second position, adjacent to the second anvil; and
   when the pinching member is in the first position, a minimum gap between the first anvil and the pinching member is less than twice a wall thickness of one of the pair of tubing lines,
   wherein each of the first and second spring members comprises an elongate flexure displaced parallel to the central axis of the shaft, each flexure having a fixed first end and a floating second end, each second end having the corresponding anvil attached thereto;
   further comprising a pair of pre-load supports, each pre-load support displaced between a corresponding fixed first end and a corresponding floating second end of the corresponding flexure for pre-loading thereof.

2. The apparatus of claim 1, wherein, when the pinching member is in the second position, a minimum gap between the second anvil and the pinching member is less than twice a wall thickness of the other of the pair of tubing lines.

3. The apparatus of claim 1, further comprising a fixed structure supporting the shaft; wherein the first fixed end of each flexure is coupled to the structure and each pre-load support is formed in the structure.

4. The apparatus of claim 1, wherein:
   the minimum gap corresponds to an approximate 20% squeeze reduction of the wall thickness of the one of the pair of tubing lines minus a maximum in-service deflection of the pre-loaded flexure; and
   the maximum in-service deflection and a spring constant of the pre-loaded flexure provide a pinching force on the one of the pair of tubing lines, when the pinching member is in the first position, of greater than approximately 45 pounds that varies within approximately 15% of nominal over the range of the maximum in-service deflection.

5. The apparatus of claim 1, wherein the pinching member is rotatably mounted about an auxiliary axis that is offset from the central axis of the shaft.

6. The apparatus of claim 1, wherein each anvil has a radius between approximately 0.06 inch (1.5 mm) and approximately 0.08 inch (2 mm).

7. A valve apparatus for controlling flow through a tubing line of a medical injection system, the apparatus comprising:
   a rotatable shaft;
   a pinching member coupled to the rotatable shaft such that the pinching member moves around a central axis of the shaft when the shaft is rotated; and
   an anvil attached to a spring member and located alongside the shaft;
   wherein rotation of the shaft moves the pinching member between a neutral position and a pinching position, the pinching position being adjacent to the anvil; and
   when the pinching member is in the pinching position, a minimum gap between the anvil and the pinching member is less than twice a wall thickness of the tubing line,
   wherein the spring member comprises an elongate flexure displaced parallel to the central axis of the shaft, the flexure having a fixed first end and a floating second end, the second end having the anvil attached thereto;

further comprising a pre-load support, the pre-load support located between the fixed first end and the floating second end of the flexure for pre-loading thereof.

8. The apparatus of claim 7, further comprising a fixed structure supporting the shaft; wherein the first fixed end of the flexure is coupled to the structure and the pre-load support is formed in the structure.

9. The apparatus of claim 7, wherein
the minimum gap corresponds to an approximate 20% squeeze reduction of the wall thickness of the tubing line minus a maximum in-service deflection of the pre-loaded flexure; and
the maximum in-service deflection and a spring constant of the pre-loaded flexure provide a pinching force on the tubing line, when the pinching member is in the pinching position, of greater than approximately 45 pounds that varies within approximately 15% of nominal over the range of the maximum in-service deflection.

10. The apparatus of claim 7, wherein the pinching member is rotatably mounted about an auxiliary axis that is offset from the central axis of the shaft.

11. The apparatus of claim 7, wherein the anvil has a radius between approximately 0.06 inch (1.5 mm) and approximately 0.08 inch (2 mm).

* * * * *